United States Patent [19]

Mittleman et al.

[11] 4,332,247
[45] Jun. 1, 1982

[54] ADMINISTRATION SET INCLUDING BURETTE WITH PIVOTABLE AIR VALVE

[75] Inventors: Herbert Mittleman, Deerfield; Gordon P. Boland, Lake Zurich, both of Ill.

[73] Assignee: Baxter Travenol Laboratories, Inc., Deerfield, Ill.

[21] Appl. No.: 170,399

[22] Filed: Jul. 21, 1980

Related U.S. Application Data

[63] Continuation of Ser. No. 938,063, Aug. 30, 1978, abandoned.

[51] Int. Cl.³ .............................................. A61M 5/14
[52] U.S. Cl. ............................ 128/214 C; 128/214 R
[58] Field of Search ............... 128/214 R, 214 C, 272; 222/481, 482; 215/247, 248

[56] References Cited

U.S. PATENT DOCUMENTS

| | | | |
|---|---|---|---|
| 1,277,825 | 9/1918 | Baker | 215/312 |
| 3,398,926 | 8/1968 | Scaramucci | 251/309 |
| 3,709,254 | 1/1973 | Wright | |
| 3,776,229 | 12/1973 | McPhee | 125/214 C |
| 3,855,997 | 12/1974 | Sauer | 215/309 |
| 3,896,733 | 7/1975 | Rosenberg | 128/214 R |
| 3,976,068 | 8/1976 | Lundquist | 128/214 R |

FOREIGN PATENT DOCUMENTS 224608 10/1959 Australia ............................ 128/272

Primary Examiner—Robert W. Michell
Assistant Examiner—Nancy A. B. Swisher
Attorney, Agent, or Firm—Paul C. Flattery; John P. Kirby, Jr.; George H. Gerstman

[57] ABSTRACT

An administration set including a burette with an air valve communicating with the burette chamber. The air valve comprises a stationary port extending from a top portion of the burette chamber with a fitting closing the port except for a small passageway defined by a top portion of the fitting. A pivotable closure overlies the port and is pivotally connected therewith. The pivotable closure defines an opening for communication with the small passageway when the closure is pivoted to a predetermined open position. The closure opening and the passageway are segregated when the closure is not in the predetermined open position. A filter member is received within the port and directly underlies the small passageway.

9 Claims, 6 Drawing Figures

ADMINISTRATION SET INCLUDING BURETTE WITH PIVOTABLE AIR VALVE

This is a continuation of application Ser. No. 938,063, filed Aug. 30, 1978 now abandoned.

BACKGROUND OF THE INVENTION

This invention concerns an administration set of the type used for dispensing parenteral liquid to a patient, and, more particularly, to an administration set including a burette having a pivotable air valve.

Administration sets including burettes with drip chambers are widely used for administering parenteral liquids to a patient. The burettes typically include a burette chamber with a primary liquid inlet to the chamber and also an injection site communicating with the chamber for injecting medicament into the chamber so that, for example, the medicament may be diluted with the primary liquid.

When the burette is being filled with liquid or medicament is being injected into the burette for dilution with the liquid, communication of the burette chamber with the air outside the chamber is necessary. To this end, in one prior art administration set construction, an air tube communicates with the burette chamber, with the air tube having a filter at one end and a clamp between the filter and the burette chamber. When it is desired for burette chamber to be open to air, the clamp is opened.

In another prior art construction, as disclosed in McPhee U.S. Pat. No. 3,776,229, a rotatable air valve communicates with the burette chamber for providing the necessary air vent. However, the rotary air valve disclosed in this patent has certain disadvantages. For example, because of the grooved construction of the system, the rotatable portion of the air valve can be easily pulled off by an operator. Additionally, it has been found that the air valve disclosed in this patent generally requires silicone lubricant in order to provide adequate sealing properties when the valve is closed. This is disadvantageous because the silicone lubricant may become introduced into the burette. Further, the filter carried within the air valve may become clogged, particularly when the unit is shaken by the operator, and there is no way to unclog the filter once it becomes clogged.

Accordingly, it is an object of the present invention to provide an administration set having a burette which obviates the requirement for an air tube extending from the burette chamber with a clamp between the air filter and the burette chamber.

Another object of the present invention is to provide an administration set with a burette having a pivotable air valve of the type that cannot be easily removed by an operator.

A further object of the present invention is to provide an administration set having a burette which uses an air valve that does not require silicone lubrication.

A still further object of the present invention is to provide an administration set having an air valve which is structurally arranged to allow an operator to at least partially unclog the filter carried by the air valve, if the filter should become clogged.

Other objects and advantages of the present invention will become apparent as the description proceeds.

SUMMARY OF THE INVENTION

In accordance with the present invention, an administration set is provided of the type including a burette having a burette chamber and a main liquid inlet, an injection site and an air valve communicating with the chamber, and a drip chamber connected downstream of the burette chamber. The improvement comprises the air valve comprising a stationary port extending from a top portion of the burette chamber and defining a bore therethrough. The port includes a fitting defining an open internal portion with the fitting closing the port except for a passageway defined by a top portion of the fitting. The passageway is substantially smaller than the open internal portion.

A pivotable closure overlies the port and is pivotally connected therewith. The pivotable closure defines an opening for communication with the passageway when the closure is pivoted to a predetermined open position.

Means are provided for segregating the closure opening and the passageway when the closure is not in its predetermined open position. A filter member is located transverse the bore and directly underlies the passageway.

In the illustrative embodiment, the stationary port comprises an open annular member and a separate fitting fastened to the open annular member. The pivotal connection is between the separate fitting and the pivotable closure and comprises a circular flange and cooperating groove arrangement with the fitting carrying a flange and the closure defining a cooperating groove. The pivotable closure includes an arm extending therefrom to provide manual grasping and the closure and stationary port have a secure pivotal connection preventing an operator from removing the closure from the port.

In the illustrative embodiment, the segregating means comprise a resilient member movable with a pivoting member of the closure, to close and seal the passageway when the closure is not in the predetermined open position. The resilient member comprises a ball carried by the closure and spaced from the opening defined by the closure, and the fitting defines an inclined groove for receiving the ball when the closure is pivoted to its predetermined open positon. The inclined groove is dimensioned so as to enable the ball to not be under compression when the closure is in its predetermined open position, and so as to enable the ball to move up the incline when the closure is pivoted to a closed position, to place the ball under compression, sealing the passageway when the closure is in a closed position.

A more detailed explanation of the invention is provided in the following description and claims, and is illustrated in the accompanying drawings.

DETAILED DESCRIPTION OF THE ILLUSTRATIVE EMBODIMENT

Figure 1:
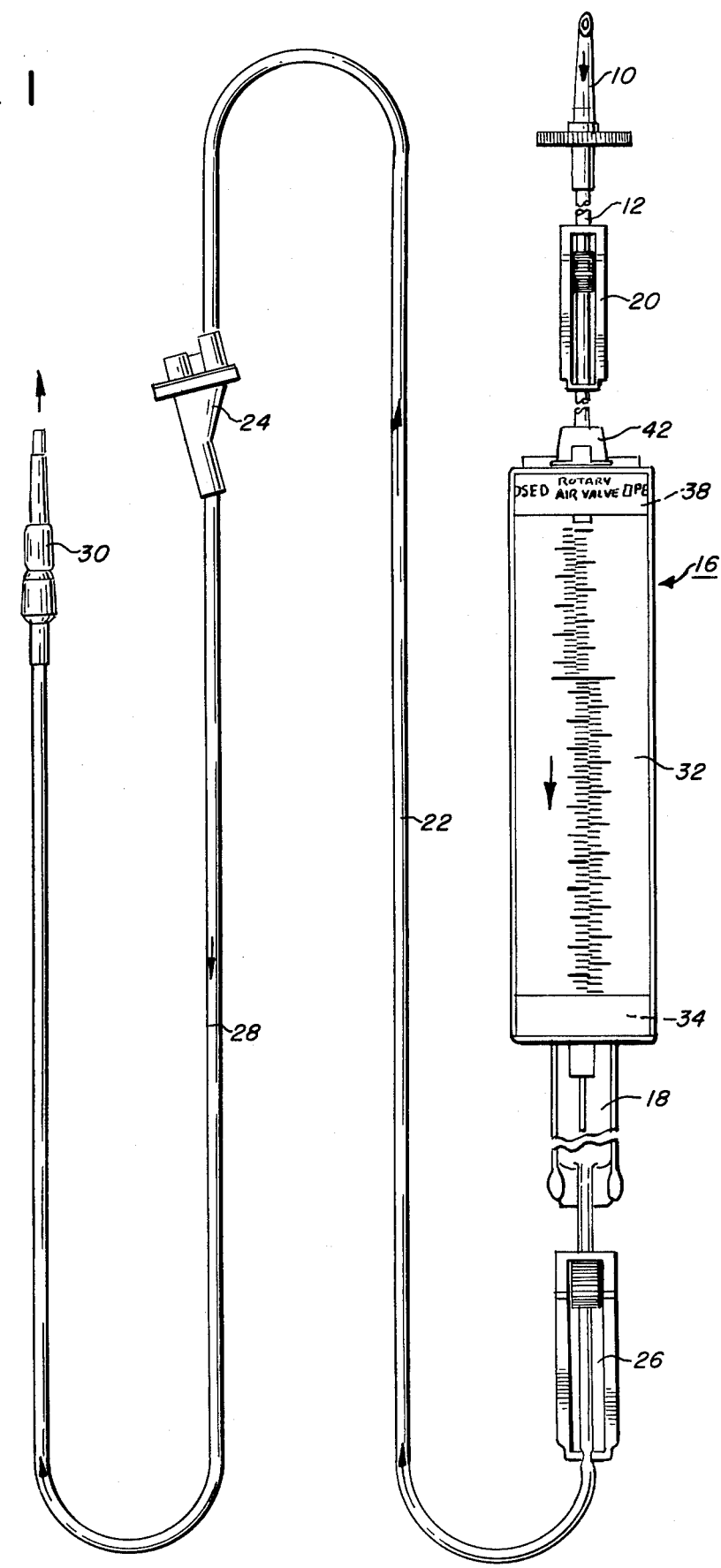
FIG. 1 is a view of an administration set constructed in accordance with the principles of the present invention.
Figure 2:
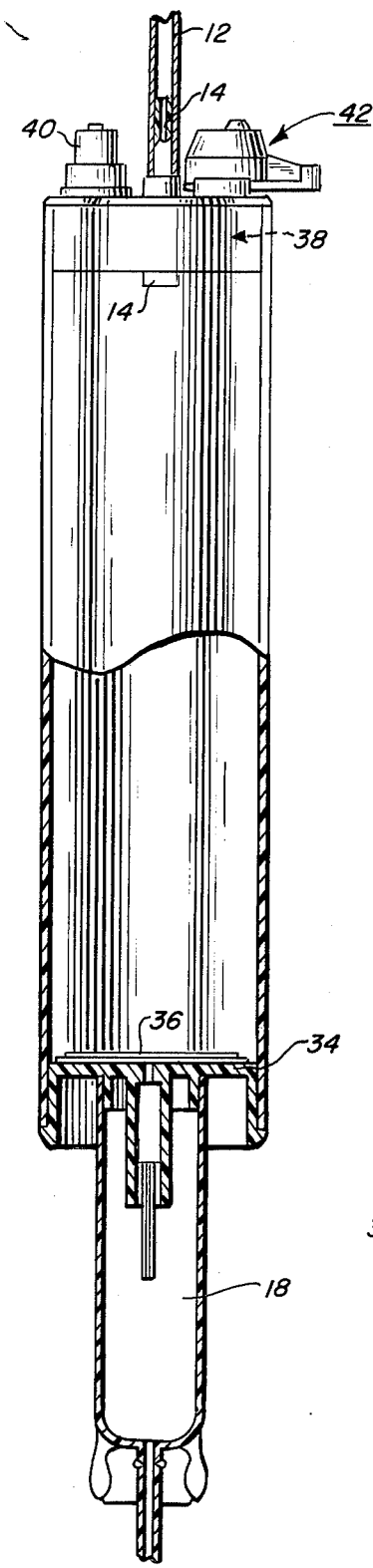
FIG. 2 is a front view, partially broken for clarity, of a burette and associated drip chamber used in connection with the administration set of FIG. 1.

Referring to FIG. 1, an administration set constructed in accordance with the principles of the present invention is shown therein. The administration set includes a conventional spike 10 for coupling to a source of parenteral liquid, tubing 12 connected to main liquid inlet 14 (FIG. 4) of a burette 16, the burette having a drip chamber 18 extending from the bottom thereof and in series with the flow line, a roller clamp 20, tubing 22 connected from drip member 18 to an injection site 24, roller clamp 26 on tubing 22, and tubing 28 connected from the outlet of injection site 24 to a conventional needle adapter 30.

Referring now to FIGS. 1-4, the burette 16 includes a burette chamber 32 having a platform 34 at its outlet end supporting a filter 36, and having an inlet assembly 38 at its inlet end. Inlet assembly 38 includes main liquid inlet 14 of conventional construction, an injection site 40 of conventional construction, and a novel pivotable air valve 42.

Figure 4:
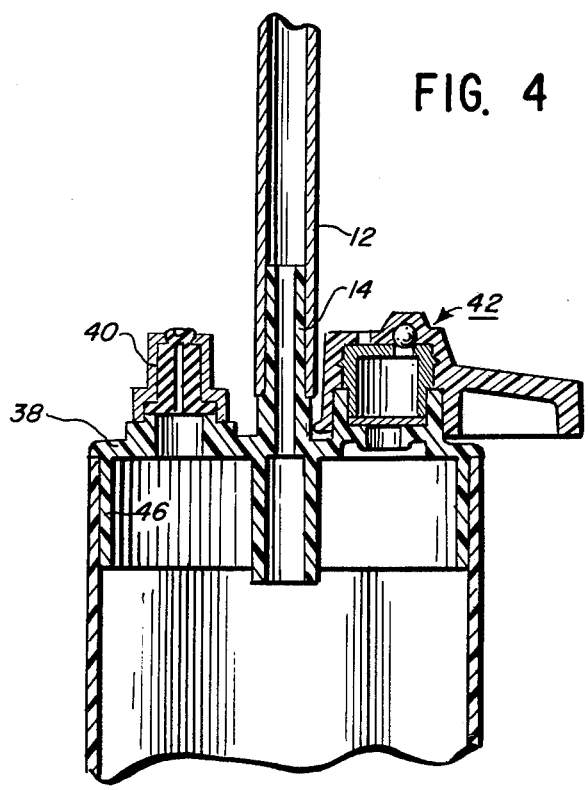
FIG. 4 is a cross-sectional view thereof, taken along the plane of the line 4—4 of FIG. 3.
Figure 5:
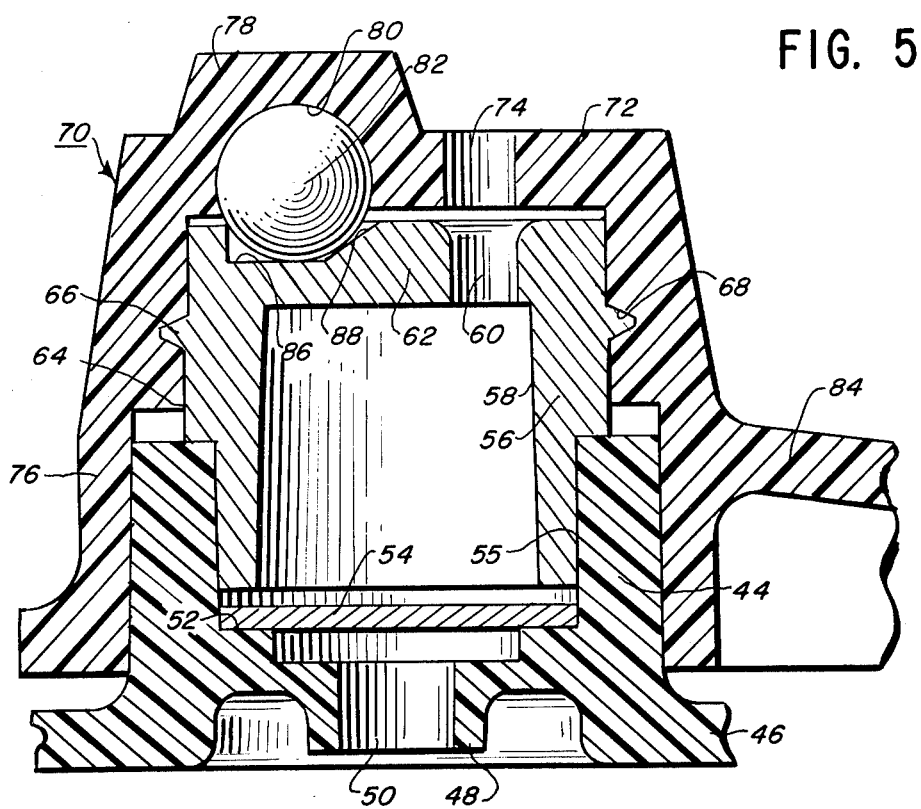
FIG. 5 is a greatly enlarged, fragmentary, cross-sectional view of the pivotable air vent in its predetermined open position.
Figure 6:
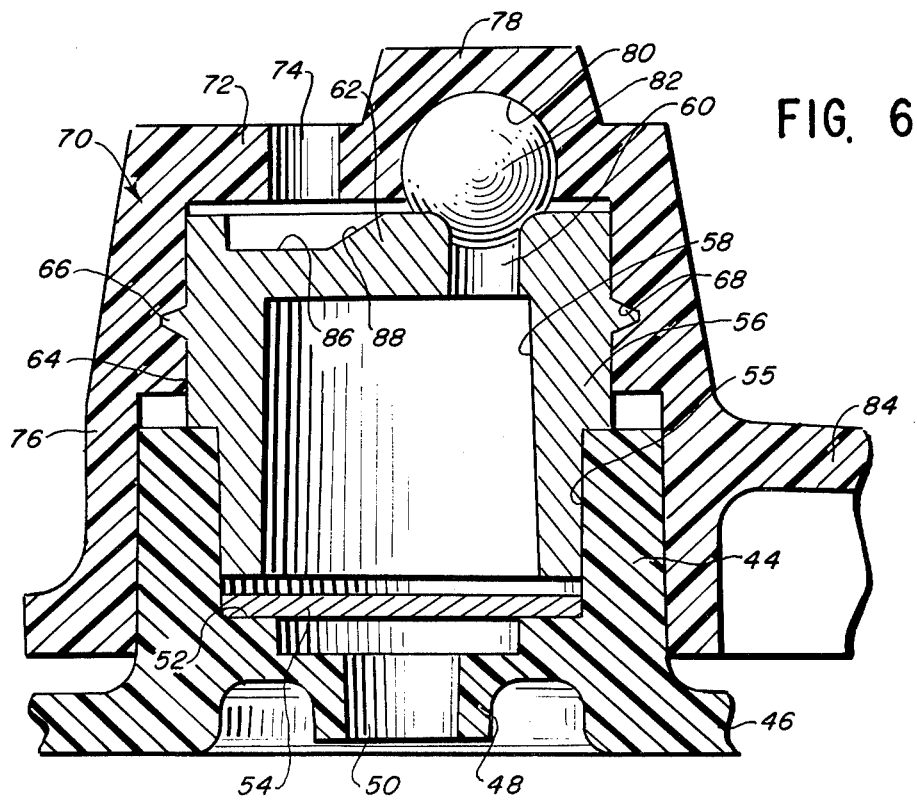
FIG. 6 is a greatly enlarged, fragmentary view thereof, with the pivotable valve shown in a closed position.

Air valve 42 is shown in detail in FIGS. 4-6. As illustrated therein, the air valve includes an upstanding annular stationary port 44, which in the illustrative embodiment is formed integrally with the base 46 of inlet assembly 38. Port 44 carries a central member 48 which defines an axial bore 50. Port 44 also defines a shoulder 52 which supports air filter 54. Air filter 54 is preferably circular and dimensioned so as to fit securely in a resting position on shoulder 52.

Within the internal wall 55 of port 54, there is pressure-fitted a fitting 56 which defines an open internal portion 58 and closes port 44 except for a passageway 60. Passageway 60 is defined by the top portion 62 of fitting 56 and the passageway is much smaller than the open internal portion 58.

The external sidewall 64 of fitting 56 carries an annular flange 66 which cooperates with an internal groove 68 of a pivotable closure 70, to form a pivotal connection between pivotable closure 70 and stationary fitting 56.

Pivotable closure 70 comprises a top wall 72 defining an opening 74 for communication with passageway 60 when the closure is pivoted to a predetermined open position, and an annular sidewall 76 which extends downwardly and externally of port 44. Sidewall 76 is dimensioned so that when the pivotable closure 70 is snapped onto fitting 56, there is a relatively close fit between the internal surfaces of sidewall 76 and the external surfaces of fitting 56 and port 44. However, the coupling is such that the pivotable closure 70 can rotate with respect to stationary port 44 and fitting 56.

Pivotable closure 70 also has a raised portion 78 which defines an arc 80 for receiving a resilient ball 82. Resilient ball 82 is preferably a silicone rubber sphere which is utilized to seal passageway 60 when the closure 70 is not in its predetermined open position. Closure 70 also carries a radially extending, manually-graspable handle 84 for enabling the operator to pivot the closure easily.

As shown in FIGS. 5 and 6, fitting 56 defines a groove 86 having an incline 88, which incline leads to the top of passageway 60. As illustrated in FIG. 5, when the closure 70 is in its predetermined open position, ball 82 will lie within groove 86 and opening 74 will be aligned with passageway 60. Arc 80 and groove 86 are dimensioned so that ball 82 will not be in a compressed state in its position illustrated in FIG. 5. When arm 84 is turned so that closure 70 is not in its predetermined open position, ball 82 will be moved to seal passageway 60 as illustrated in FIG. 6. In this position, the ball 80 is under compression to provide an effective seal.

By utilizing the aforementioned construction, a highly effective pivotable air valve is provided. The pivotable closure is securely pivotally connected to the stationary portion, the use of silicone lubricant to provide adequate sealing properties is unnecessary and if filter 54 is clogged, a needle can be inserted through opening 74 and passageway 60 to at least partially unclog the filter, as the filter directly underlies passageway 60.

Figure 3:
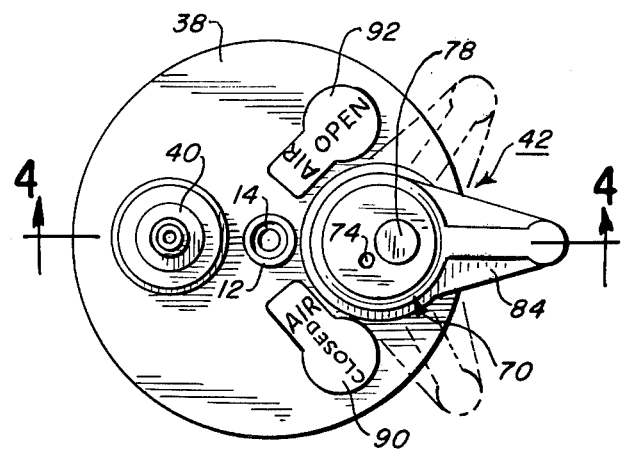
FIG. 3 is a top view of the burette of FIG. 2, with possible movement of the pivotable valve illustrated in phantom lines.

As shown in FIG. 3, a stop member 90 is connected to the assembly for limiting the pivotal movement of closure 70 and a stop member 92 is also provided for limiting the pivotal movement of the closure 70 in the opposite direction.

Although an illustrative embodiment of the invention has been shown and described, it is to be understood that various modifications and substitutions may be made by those skilled in the art without departing from the novel spirit and scope of the present invention.

What is claimed is:

1. In an administration set including a burette having a burette chamber and a main liquid inlet, an injection site and an air valve communicating with said chamber, and a drip chamber connected downstream of the burette chamber, the improvement comprising, in combination:

said air valve comprising a stationary port extending from a top portion of said burette chamber and defining a bore therethrough;

said port including a fitting shaped to define an open internal portion, a top portion of said fitting shaped to define a passageway, said fitting closing said port except for said passageway, with said passageway being substantially smaller than said open internal portion;

a pivotable closure overlying said port and being pivotally connected therewith, said pivotable closure shaped to define an opening for communication with said passageway when said closure is pivoted to a predetermined open position; and means for segregating said closure opening and said passageway when said closure is not in said predetermined open position; and a filter member located transverse said bore and directly underlying said passageway, said segregating means comprising a resilient member movable with the pivoting movement of said closure, to close and seal said passageway when the closure is not in said predetermined open position, said resilient member comprising a ball carried by said closure and spaced from said opening defined by said closure.

2. A device as described in claim 1, said fitting defining an inclined groove for receiving said ball when the closure is pivoted to its predetermined open position.

3. A device as described in claim 1, said ball comprising a silicone rubber sphere.

4. A device as described in claim 2, said inclined groove being dimensioned so as to enable said ball to not be under compression when the closure is in its predetermined open position, and so as to enable said ball to move up the incline when the closure is pivoted to a closed position, to place the ball under compression, sealing said passageway when the closure is in a closed position.

5. In an administration set including a burette having a burette chamber and a main liquid inlet, an injection site and an air valve communicating with said chamber, and a drip chamber connected downstream of the burette chamber, the improvement comprising, in combination:

said air valve comprising a stationary port extending from a top portion of said burette chamber and defining a bore therethrough, said stationary port comprising an open annular member and a separate fitting fastened to said open annular member, said fitting shaped to define an open internal portion, a top portion of said fitting shaped to define a passageway, said fitting closing said port except for said passageway, with said passageway being substantially smaller than said open internal portion;

a pivotable closure overlying said port and being pivotally connected therewith, said pivotable connection being between said separate fitting and said pivotable closure and comprising a circular flange and cooperating groove arrangement with one of said fitting and closure carrying a flange and the other of said fitting and closure defining the cooperating groove;

said pivotable closure shaped to define an opening for communication with said passageway when said closure is pivoted to a predetermined open position;

means for segregating said closure opening and said passageway when said closure is not in said predetermined open position; and a filter member located transverse said bore and directly underlying said passageway;

said segregating means comprising a resilient member movable with the pivoting movement of said closure, to close and seal said passageway when the closure is not in said predetermined open position, said resilient member comprising a ball carried by said closure and spaced from said opening defined by said closure.

6. A device as described in claim 5, said fitting defining an inclined groove for receiving said ball when the closure is pivoted to its predetermined open position.

7. A device as described in claim 6, said inclined groove being dimensioned so as to enable said ball to not be under compression when the closure is in its predetermined open position, and so as to enable said ball to move up the incline when the closure is pivoted to a closed position, to place the ball under compression, sealing said passageway when the closure is in a closed position.

8. In an administration set including a burette having a burette chamber and a main liquid inlet, an injection site and an air valve communicating with said chamber, and a drip chamber connected downstream of the buretter chamber, the improvement comprising, in combination:

said air valve comprising a stationary port extending from a top portion of said burette chamber and defining a bore therethrough, said stationary port comprising an open annular member and a separate fitting fastened to said open annular member;

said fitting shaped to define an open internal portion, a top portion of said fitting shaped to define a passageway, said fitting closing said port except for said passgeway, with said passageway being substantially smaller than said open internal portion;

a pivotable closure overyling said port and being pivotally connected therewith, said pivotable closure shaped to define an opening for communication with said passageway when said closure is pivoted to a predetermined open position, said pivotable connection being between said separate fitting and said pivotable closure and comprising a circular flange and cooperating groove arrangement with one of said fitting and closure carrying a flange and the other of said fitting and closure defining the cooperating groove;

means for segregating said closure opening and said passageway when said closure is not in said predetermined open position, said segregating means comprising a resilient ball movable with the pivoting movement of said closure, to close and seal said passageway when the closure is not in said predetermined open position, said fitting defining an inclined groove for receiving said ball when the closure is pivoted to its predetermined open position, said fitting defining an inclined groove for receiving said ball when the closure is pivoted to its predetermined open position, said inclined groove being dimensioned so as to enable said ball to not be under compression when the closure is in its predetermined open position, and so as to enable said ball to move up the incline when the closure is pivoted to a closed position, to place the ball under compression, sealing said passageway when the closure is in a closed position; and a filter member located transverse said bore and directly underlying said passageway, said port defining support means for receiving and supporting said filter member.

9. A device as described in claim 8, said closure opening being located to directly overlie said passageway when said closure is in its predetermined open position.

* * * * *